(12) United States Patent
Luna et al.

(10) Patent No.: US 12,350,160 B2
(45) Date of Patent: Jul. 8, 2025

(54) MODULAR IMPLANT WITH EXTERNAL FIXATION

(71) Applicant: WRIGHT MEDICAL TECHNOLOGY, INC., Memphis, TN (US)

(72) Inventors: Ramon Luna, Arlington, TN (US); Johnny McGee, Halls, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 121 days.

(21) Appl. No.: 17/660,489

(22) Filed: Apr. 25, 2022

(65) Prior Publication Data

US 2022/0387177 A1 Dec. 8, 2022

Related U.S. Application Data

(60) Provisional application No. 63/208,069, filed on Jun. 8, 2021.

(51) Int. Cl.
*A61F 2/42* (2006.01)
*A61B 17/68* (2006.01)
(Continued)

(52) U.S. Cl.
CPC .......... *A61F 2/30734* (2013.01); *A61B 17/68* (2013.01); *A61B 17/72* (2013.01); *A61B 17/8685* (2013.01); *A61F 2002/30405* (2013.01); *A61F 2002/30604* (2013.01); *A61F 2002/30774* (2013.01);
(Continued)

(58) Field of Classification Search
CPC ............ A61F 2002/4205; A61F 2/4202; A61F 2002/30859; A61F 2002/30861; A61F 2/30734; A61F 2002/30405; A61F 2002/30774; A61F 2002/30845; A61F 2002/30886; A61B 17/68; A61B 17/72
See application file for complete search history.

(56) References Cited

U.S. PATENT DOCUMENTS 3,839,742 A 10/1974 Link
3,872,519 A 3/1975 Giannestras et al.
(Continued)

FOREIGN PATENT DOCUMENTS

CA 2836651 3/2016
DE 10156311 A1 * 6/2003 ........... A61B 17/686
(Continued)

OTHER PUBLICATIONS

Extended European Search Report issued in connection with Application No. 22170278.0, Oct. 12, 2022, 7 pages.
(Continued)

*Primary Examiner* — Bruce E Snow
(74) *Attorney, Agent, or Firm* — DUANE MORRIS LLP

(57) ABSTRACT

An apparatus includes a body extending from a first end to a second end. The first end is a leading end, and the second end includes a first coupling element configured to couple the body to a first other component. The body includes an external fixation element extending along a length of the first component. The external fixation element is configured to engage bone. Systems and methods are also disclosed.

30 Claims, 7 Drawing Sheets

(51) Int. Cl.
*A61B 17/72* (2006.01)
*A61B 17/86* (2006.01)
*A61F 2/30* (2006.01)
(52) U.S. Cl.
CPC .............. *A61F 2002/30845* (2013.01); *A61F 2002/30851* (2013.01); *A61F 2002/30859* (2013.01); *A61F 2002/30861* (2013.01); *A61F 2002/30881* (2013.01); *A61F 2002/30886* (2013.01); *A61F 2002/4205* (2013.01); *A61F 2220/0016* (2013.01)

(56) References Cited

U.S. PATENT DOCUMENTS

| | | | |
|---|---|---|---|
| 3,886,599 A | 6/1975 | Schlein |
| 3,889,300 A | 6/1975 | Smith |
| 3,896,502 A | 7/1975 | Lennox |
| 3,896,503 A | 7/1975 | Freeman et al. |
| 3,975,778 A | 8/1976 | Newton, III |
| 3,987,500 A | 10/1976 | Schlein |
| 4,021,864 A | 5/1977 | Waugh |
| 4,069,518 A | 1/1978 | Groth, Jr. et al. |
| 4,156,944 A | 6/1979 | Schreiber et al. |
| 4,166,292 A | 9/1979 | Bokros |
| 4,204,284 A | 5/1980 | Koeneman |
| 4,232,404 A | 11/1980 | Samuelson et al. |
| 4,309,778 A | 1/1982 | Buechel et al. |
| 4,470,158 A | 9/1984 | Pappas et al. |
| 4,755,185 A | 7/1988 | Tarr |
| 4,968,316 A | 11/1990 | Hergenroeder |
| 5,041,139 A | 8/1991 | Brånemark |
| 5,312,412 A | 5/1994 | Whipple |
| 5,326,365 A | 7/1994 | Alvine |
| 5,354,300 A | 10/1994 | Goble et al. |
| 5,423,825 A | 6/1995 | Levine |
| 5,476,466 A | 12/1995 | Barrette et al. |
| 5,601,563 A | 2/1997 | Burke et al. |
| 5,628,749 A | 5/1997 | Vendrely et al. |
| 5,634,927 A | 6/1997 | Houston et al. |
| 5,667,511 A | 9/1997 | Vendrely et al. |
| 5,674,223 A | 10/1997 | Cipolletti et al. |
| 5,735,904 A | 4/1998 | Pappas |
| 5,766,259 A | 6/1998 | Sammarco |
| 5,776,200 A | 7/1998 | Johnson et al. |
| 5,817,097 A | 10/1998 | Howard et al. |
| 5,824,106 A | 10/1998 | Fournal |
| 5,879,389 A | 3/1999 | Koshino |
| 5,885,299 A | 3/1999 | Winslow et al. |
| 5,888,203 A | 3/1999 | Goldberg |
| 5,897,559 A | 4/1999 | Masini |
| 5,935,132 A | 8/1999 | Bettuchi et al. |
| 6,002,859 A | 12/1999 | DiGioia, III et al. |
| 6,033,405 A | 3/2000 | Winslow et al. |
| 6,102,952 A | 8/2000 | Koshino |
| 6,183,519 B1 | 2/2001 | Bonnin et al. |
| 6,245,109 B1 | 6/2001 | Mendes et al. |
| 6,342,056 B1 | 1/2002 | Mac-Thiong et al. |
| 6,344,043 B1 | 2/2002 | Pappas |
| 6,409,767 B1 | 6/2002 | Pericé et al. |
| 6,413,260 B1 * | 7/2002 | Berrevoets ............ A61B 17/68 606/304 |
| 6,436,146 B1 | 8/2002 | Hassler et al. |
| 6,478,800 B1 | 11/2002 | Fraser et al. |
| 6,520,964 B2 | 2/2003 | Tallarida et al. |
| 6,530,930 B1 | 3/2003 | Marino et al. |
| 6,610,067 B2 | 8/2003 | Tallarida et al. |
| 6,610,095 B1 | 8/2003 | Pope et al. |
| 6,620,168 B1 | 9/2003 | Lombardo et al. |
| 6,645,215 B1 | 11/2003 | McGovern et al. |
| 6,663,669 B1 | 12/2003 | Reiley |
| 6,673,116 B2 | 1/2004 | Reiley |
| 6,679,917 B2 | 1/2004 | Ek |
| 6,719,799 B1 | 4/2004 | Kropf |
| 6,824,567 B2 | 11/2004 | Tornier et al. |
| 6,852,130 B2 | 2/2005 | Keller et al. |
| 6,860,902 B2 | 3/2005 | Reiley |
| 6,863,691 B2 | 3/2005 | Short et al. |
| 6,875,222 B2 | 4/2005 | Long et al. |
| 6,875,236 B2 | 4/2005 | Reiley |
| 6,926,739 B1 | 8/2005 | O'Connor et al. |
| 6,939,380 B2 | 9/2005 | Guzman |
| 6,942,670 B2 | 9/2005 | Heldreth et al. |
| 7,001,394 B2 | 2/2006 | Gundlapalli et al. |
| 7,011,687 B2 | 3/2006 | Deffenbaugh et al. |
| 7,025,790 B2 | 4/2006 | Parks et al. |
| 7,163,541 B2 | 1/2007 | Ek |
| 7,238,190 B2 | 7/2007 | Schon et al. |
| 7,252,684 B2 | 8/2007 | Dearnaley |
| 7,314,488 B2 | 1/2008 | Reiley |
| 7,323,012 B1 | 1/2008 | Stone et al. |
| 7,476,227 B2 | 1/2009 | Tornier et al. |
| 7,481,814 B1 | 1/2009 | Metzger |
| 7,485,147 B2 | 2/2009 | Papps et al. |
| 7,534,246 B2 | 5/2009 | Reiley et al. |
| 7,534,270 B2 | 5/2009 | Ball |
| 7,615,082 B2 | 11/2009 | Naegerl et al. |
| 7,618,421 B2 | 11/2009 | Axelson, Jr. et al. |
| 7,625,409 B2 | 12/2009 | Saltzman et al. |
| 7,641,697 B2 | 1/2010 | Reiley |
| 7,678,151 B2 | 3/2010 | Ek |
| 7,713,305 B2 | 5/2010 | Ek |
| 7,717,920 B2 | 5/2010 | Reiley |
| 7,763,080 B2 | 7/2010 | Southworth |
| 7,803,158 B2 | 9/2010 | Hayden |
| 7,850,698 B2 | 12/2010 | Straszheim-Morley et al. |
| 7,896,883 B2 | 3/2011 | Ek et al. |
| 7,896,885 B2 | 3/2011 | Miniaci et al. |
| 7,909,882 B2 | 3/2011 | Stinnette |
| 7,963,996 B2 | 6/2011 | Saltzman et al. |
| 8,002,841 B2 | 8/2011 | Hasselman |
| 8,012,217 B2 | 9/2011 | Strzepa et al. |
| 8,034,114 B2 | 10/2011 | Reiley |
| 8,034,115 B2 | 10/2011 | Reiley |
| 8,048,164 B2 | 11/2011 | Reiley |
| 8,110,006 B2 | 2/2012 | Reiley |
| 8,114,091 B2 | 2/2012 | Ratron et al. |
| 8,167,888 B2 | 5/2012 | Steffensmeier |
| 8,172,850 B2 | 5/2012 | McMinn |
| 8,177,841 B2 | 5/2012 | Ek |
| 8,268,007 B2 | 9/2012 | Barsoum et al. |
| 8,303,667 B2 | 11/2012 | Younger |
| 8,313,492 B2 | 11/2012 | Wong et al. |
| 8,317,797 B2 | 11/2012 | Rasmussen |
| 8,323,346 B2 | 12/2012 | Tepic |
| 8,337,503 B2 | 12/2012 | Lian |
| 8,361,159 B2 | 1/2013 | Ek |
| 8,475,463 B2 | 7/2013 | Lian |
| 8,491,596 B2 | 7/2013 | Long et al. |
| 8,808,303 B2 | 8/2014 | Stemniski et al. |
| 8,911,444 B2 | 12/2014 | Bailey |
| 9,282,977 B2 * | 3/2016 | Penzimer ............ A61B 17/1682 |
| 9,610,109 B2 * | 4/2017 | Weiss ................... A61B 17/68 |
| 9,907,561 B2 | 3/2018 | Luna et al. |
| 10,034,678 B2 | 7/2018 | Park et al. |
| 10,039,558 B2 | 8/2018 | Park et al. |
| 10,206,688 B2 | 2/2019 | Park et al. |
| 2002/0068977 A1 | 6/2002 | Jackson |
| 2002/0082607 A1 | 6/2002 | Heldreth et al. |
| 2002/0133164 A1 | 9/2002 | Williamson |
| 2002/0173853 A1 | 11/2002 | Corl, III et al. |
| 2003/0078669 A1 | 4/2003 | Martin et al. |
| 2003/0208280 A1 | 11/2003 | Tohidi |
| 2003/0236522 A1 | 12/2003 | Long et al. |
| 2004/0030399 A1 | 2/2004 | Asencio |
| 2004/0039394 A1 | 2/2004 | Conti et al. |
| 2004/0068322 A1 | 4/2004 | Ferree |
| 2004/0167631 A1 | 8/2004 | Luchesi et al. |
| 2004/0186585 A1 | 9/2004 | Feiwell |
| 2004/0216259 A1 | 11/2004 | Ponziani |
| 2004/0236431 A1 | 11/2004 | Sekel |
| 2005/0004676 A1 | 1/2005 | Schon et al. |
| 2005/0165408 A1 | 7/2005 | Puno et al. |
| 2005/0192674 A1 | 9/2005 | Ferree |
| 2006/0009857 A1 | 1/2006 | Gibbs et al. |

(56) References Cited

U.S. PATENT DOCUMENTS

| | | |
|---|---|---|
| 2006/0020345 A1 | 1/2006 | O'Connor et al. |
| 2006/0036257 A1 | 2/2006 | Steffensmeier |
| 2006/0116679 A1 | 6/2006 | Lutz et al. |
| 2006/0142870 A1 | 6/2006 | Robinson et al. |
| 2006/0235541 A1 | 10/2006 | Hodorek |
| 2006/0247788 A1 | 11/2006 | Ross |
| 2007/0038303 A1 | 2/2007 | Myerson et al. |
| 2007/0100346 A1 | 5/2007 | Wyss et al. |
| 2007/0112431 A1 | 5/2007 | Kofoed |
| 2007/0162025 A1 | 7/2007 | Tornier et al. |
| 2007/0173944 A1 | 7/2007 | Keller et al. |
| 2007/0173947 A1 | 7/2007 | Ratron |
| 2007/0213830 A1 | 9/2007 | Ammann et al. |
| 2007/0233129 A1 | 10/2007 | Bertagnoli et al. |
| 2007/0276400 A1 | 11/2007 | Moore et al. |
| 2007/0288030 A1 | 12/2007 | Metzger et al. |
| 2008/0015602 A1 | 1/2008 | Axelson |
| 2008/0097617 A1 | 4/2008 | Fellinger et al. |
| 2008/0103603 A1 | 5/2008 | Hintermann |
| 2008/0109081 A1 | 5/2008 | Bao et al. |
| 2008/0195233 A1 | 8/2008 | Ferrari et al. |
| 2008/0215156 A1 | 9/2008 | Duggal et al. |
| 2008/0287954 A1 | 11/2008 | Kunz et al. |
| 2008/0312745 A1 | 12/2008 | Keller et al. |
| 2009/0018660 A1* | 1/2009 | Roush ............... A61F 2/30988 606/104 |
| 2009/0024131 A1 | 1/2009 | Metzger et al. |
| 2009/0043310 A1 | 2/2009 | Rasmussen |
| 2009/0054992 A1 | 2/2009 | Landes et al. |
| 2009/0082875 A1 | 3/2009 | Long |
| 2009/0105767 A1 | 4/2009 | Reiley |
| 2009/0105840 A1 | 4/2009 | Reiley |
| 2009/0182433 A1 | 7/2009 | Reiley et al. |
| 2009/0198341 A1 | 8/2009 | Choi et al. |
| 2009/0234360 A1 | 9/2009 | Alexander |
| 2009/0276052 A1 | 11/2009 | Regala et al. |
| 2010/0010493 A1 | 1/2010 | Dower |
| 2010/0023066 A1 | 1/2010 | Long et al. |
| 2010/0023126 A1 | 1/2010 | Grotz |
| 2010/0057216 A1 | 3/2010 | Gannoe et al. |
| 2010/0069910 A1 | 3/2010 | Hasselman |
| 2010/0198355 A1 | 8/2010 | Kofoed et al. |
| 2010/0241237 A1 | 9/2010 | Pappas |
| 2010/0305572 A1 | 12/2010 | Saltzman et al. |
| 2010/0318088 A1 | 12/2010 | Warne et al. |
| 2010/0331984 A1 | 12/2010 | Barsoum et al. |
| 2011/0029090 A1 | 2/2011 | Zannis et al. |
| 2011/0035018 A1 | 2/2011 | Deffenbaugh et al. |
| 2011/0035019 A1 | 2/2011 | Goswami et al. |
| 2011/0106268 A1 | 5/2011 | Deffenbaugh et al. |
| 2011/0125200 A1 | 5/2011 | Hanson et al. |
| 2011/0125275 A1 | 5/2011 | Lipman et al. |
| 2011/0125284 A1 | 5/2011 | Gabbrielli et al. |
| 2011/0152868 A1 | 6/2011 | Kourtis et al. |
| 2011/0152869 A1 | 6/2011 | Ek et al. |
| 2011/0166608 A1 | 7/2011 | Duggal et al. |
| 2011/0190829 A1 | 8/2011 | Duggal et al. |
| 2011/0218542 A1 | 9/2011 | Lian |
| 2011/0253151 A1 | 10/2011 | Tochigi et al. |
| 2011/0276052 A1 | 11/2011 | Hasselman |
| 2011/0295380 A1 | 12/2011 | Long |
| 2012/0010718 A1 | 1/2012 | Still |
| 2012/0046753 A1 | 2/2012 | Cook et al. |
| 2012/0053644 A1 | 3/2012 | Landry et al. |
| 2012/0083789 A1 | 4/2012 | Blakemore et al. |
| 2012/0109131 A1 | 5/2012 | Vasarhelyi et al. |
| 2012/0109326 A1 | 5/2012 | Perler |
| 2012/0130376 A1 | 5/2012 | Loring et al. |
| 2012/0136443 A1 | 5/2012 | Wenzel |
| 2012/0185057 A1 | 7/2012 | Abidi et al. |
| 2012/0191210 A1 | 7/2012 | Ratron et al. |
| 2012/0239045 A1 | 9/2012 | Li |
| 2012/0245701 A1 | 9/2012 | Zak et al. |
| 2012/0271430 A1 | 10/2012 | Arnett et al. |
| 2012/0277745 A1 | 11/2012 | Lizee |
| 2013/0041473 A1 | 2/2013 | Rouyer et al. |
| 2013/0116797 A1 | 5/2013 | Coulange et al. |
| 2013/0131822 A1* | 5/2013 | Lewis ............... A61B 17/7266 623/21.19 |
| 2013/0274814 A1* | 10/2013 | Weiner ............... A61B 17/7291 606/301 |
| 2013/0338722 A1* | 12/2013 | Yalizis ............... A61B 17/68 606/312 |
| 2015/0134071 A1* | 5/2015 | Luna ............... A61B 17/1682 606/62 |
| 2016/0135815 A1 | 5/2016 | Loring et al. |
| 2018/0055648 A1* | 3/2018 | Dhillon ............... A61F 2/4202 |
| 2018/0289380 A1* | 10/2018 | Mauldin ............... A61B 17/15 |
| 2018/0360512 A1* | 12/2018 | Mari ............... A61B 17/7055 |
| 2020/0038189 A1* | 2/2020 | Williams ............... A61F 2/4225 |
| 2020/0214828 A1* | 7/2020 | Diaz ............... A61B 17/0401 |
| 2020/0237415 A1* | 7/2020 | Champagne ....... A61B 17/8645 |
| 2021/0338294 A1* | 11/2021 | Zander ............... A61B 17/8635 |

FOREIGN PATENT DOCUMENTS

| | | |
|---|---|---|
| EP | 2967697 | 4/2018 |
| GB | 2480846 | 12/2011 |
| JP | H11-500035 | 1/1999 |
| JP | 2006150055 | 6/2006 |
| JP | 2007518453 | 7/2007 |
| JP | 2007519477 | 7/2007 |
| JP | 2007536011 | 12/2007 |
| JP | 2011526189 | 10/2011 |
| JP | 2012518517 | 8/2012 |
| JP | 2013500810 | 1/2013 |
| JP | 2013511358 | 4/2013 |
| JP | 2014131738 | 7/2014 |
| WO | WO 9625106 | 8/1996 |
| WO | WO 0166021 A1 | 9/2001 |
| WO | WO 2005011523 A2 | 2/2005 |
| WO | WO 2006022923 | 3/2006 |
| WO | WO 2006023824 | 3/2006 |
| WO | WO 2006099270 | 9/2006 |
| WO | WO 2007084846 | 7/2007 |
| WO | WO 2009158522 | 12/2009 |
| WO | WO 2010099142 | 9/2010 |
| WO | WO 2011015863 | 2/2011 |
| WO | WO 2011063281 | 5/2011 |
| WO | WO 2011151657 | 12/2011 |
| WO | WO 2012088036 | 6/2012 |
| WO | WO 2012116089 | 8/2012 |
| WO | 2014152308 A1 | 9/2014 |
| WO | 2017105815 A1 | 6/2017 |
| WO | 2019060780 A2 | 3/2019 |

OTHER PUBLICATIONS

Search report issued for European patent application No. 13198280 dated Feb. 5, 2014.
International Search Report for International patent application No. PCT/US2014/027448 dated Jul. 7, 2014.
International Preliminary Report on Patentability issued for International patent application No. PCT/US2014/027448, Sep. 15, 2015, 8 pages.
Partial European Search Report issued in connection with European patent application No. 14768333.8, Oct. 26, 2016, 6 pages.
Patent Examination Report No. 1 issued in connection with Australian patent application No. 2015202080, Jul. 5, 2016, 4 pages.
First Office Action issued for Japanese patent application No. 2016-117842, Sep. 12, 2017, 5 pages.
First Office Action issued in connection with corresponding Japanese Patent Application No. 2020-016447, Apr. 6, 2021, 4 pages.
Office Action in corresponding Canadian Patent Application No. 2,904,652, Jun. 2, 2020, 6 pages.
First Examination Report issued in corresponding Australian Patent Application No. 2019213412, Sep. 3, 2020, 5 pages.
First Office Action in corresponding Canadian Patent Application No. 2,904,652, Jan. 28, 2020, 5 pages.
Final Office Action issued in connection with corresponding Japanese Patent Application No. 206-502443, May 15, 2018, 3 pages.

(56) References Cited

OTHER PUBLICATIONS

Extended European Search Report issued in connection with corresponding European Patent Application No. 18160378.8, Jun. 29, 2018, 7 pages.
Second Office Action issued in connection with corresponding Chinese Patent Application No. 2018071101785100, dated Jul. 16, 2016, 6 pages.
First Office Action in corresponding Japanese Patent Application No. 2018-178853, Sep. 3, 2018, 3 pages.
Examination Report No. 1 issued in connection with corresponding Australian Patent Application No. 20182000073, Dec. 24, 2018, 3 pages.
First Office Action issued in connection with corresponding Japanese Patent Application No. 2018-092289, Mar. 5, 2019, 2 pages.
Extended European Search Report and Opinion in connection with European Patent Application No. 14768333.8, dated Jan. 30, 2017, 10 pages.
Examination Report issued in connection with corresponding European Patent Application No. 22170278.0, Feb. 3, 2025, 5 pages.

\* cited by examiner

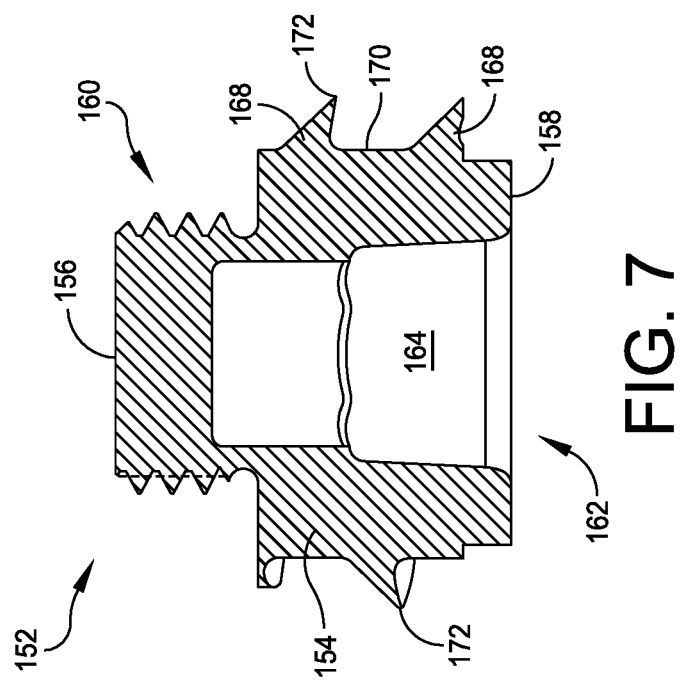
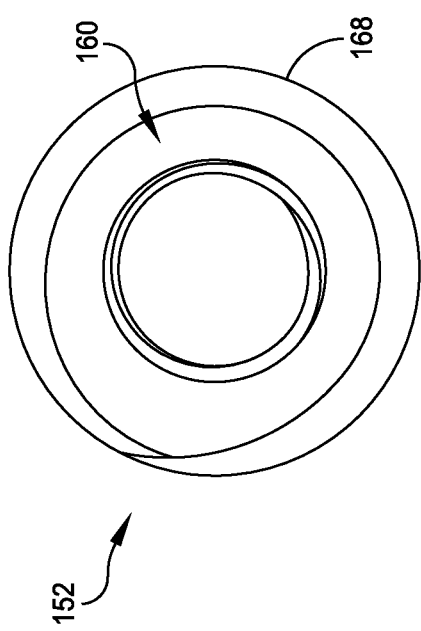
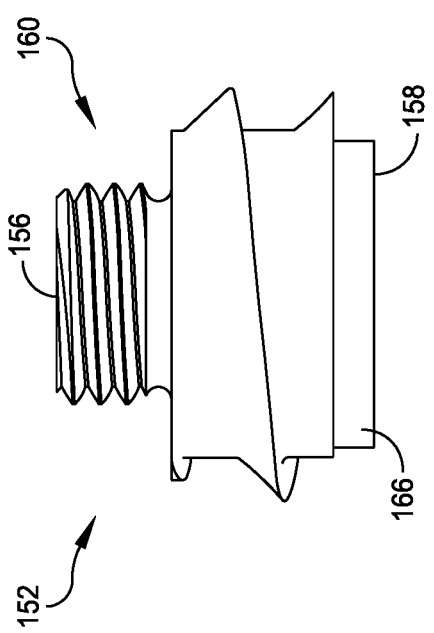

MODULAR IMPLANT WITH EXTERNAL FIXATION

CROSS-REFERENCE TO RELATED APPLICATION

This application claims priority under 35 U.S.C. § 119(e) to U.S. Provisional Application No. 63/208,069, filed Jun. 8, 2021, the entirety of which is incorporated by reference herein.

INCORPORATION BY REFERENCE

This application incorporates by reference the entireties of commonly assigned U.S. Provisional Patent Application No. 63/153,040, filed Feb. 24, 2021 (the "'040 Application"); U.S. Provisional Patent Application No. 63/169,306, filed Apr. 1, 2021 (the "306 Application"); U.S. Pat. No. 8,715,362, entitled "Ankle Replacement System" (the "'362 Patent"); and U.S. Pat. No. 9,907,561, entitled "Ankle Replacement System and Method" (the "'561 Patent").

FIELD OF DISCLOSURE

The disclosed system and method to implants. More particularly, the disclosed systems and methods relate to providing external fixation to implants received within an intramedullary canal.

BACKGROUND

Medical prostheses are available to address any number of abnormalities. For example, a prosthesis may be provided to replace a joint, such as a shoulder, elbow, knee, or ankle. Each prosthesis may include one or more components, such as a stem that is to be inserted into a passageway formed along an axis of a bone, and a tray that is to be coupled to the stem. The tray may support one or more additional components, such as an articular surface formed from metal or polymer that may be coupled to the tray. In order to speed recovery and reduce complications, surgical techniques seek to minimize the size or length of an incision or access site needed to install a prosthesis. As a result, there continues to be a need to minimize the size of the implant to be installed.

SUMMARY

In some embodiments, an apparatus includes a body extending from a first end to a second end. The first end is a leading end, and the second end includes a first coupling element configured to couple the body to a first other component. The body includes an external fixation element extending along a length of the first component. The external fixation element is configured to engage bone.

In some embodiments, a system includes a first component and a second component. The first component includes a first body having a first length extending from a first end to a second end. The first end is a leading end, and the second end includes a first coupling element. The second component includes a second body having a second length extending from a third end to a fourth end. The third end includes a second coupling element, and the fourth end including a third coupling element. At least one of the first body and the second body includes a first external fixation element configured to engage bone. The second coupling element is configured to be coupled to the first coupling element to couple the first and second components together.

In some embodiments, a method includes coupling a first coupling element provided by a first component to a second coupling element provided by a second component to couple together the first component and the second component, and inserting the first component and the second component into an intramedullary channel formed in bone such that an external fixation element extending from a body of at least the first component or the second component engages bone to fix the first component and the second component within the bone.

In some embodiments, a method includes inserting a first component into a channel formed in a first bone such that a first external fixation element extending from a body of the first component engages bone, and coupling a second component to the first component in situ by engaging a first coupling element provided by the first component with a second coupling element provided by the second component.

BRIEF DESCRIPTION OF THE DRAWINGS

The description of the exemplary embodiments disclosed herein are intended to be read in connection with the accompanying drawings, which are to be considered part of the entire written description. All drawing figures are schematic illustrations and are not intended to show actual dimensions or proportions.

FIG. 5 is a side view of a second component of the multi-component implant having external fixation illustrated in FIG. 1 in accordance with some embodiments;

FIG. 6 is a top side view of the second component illustrated in FIG. 5 in accordance with some embodiments;

FIG. 7 is a cross-sectional view of the second component illustrated in FIG. 5 in accordance with some embodiments;

DETAILED DESCRIPTION

Figure 1:
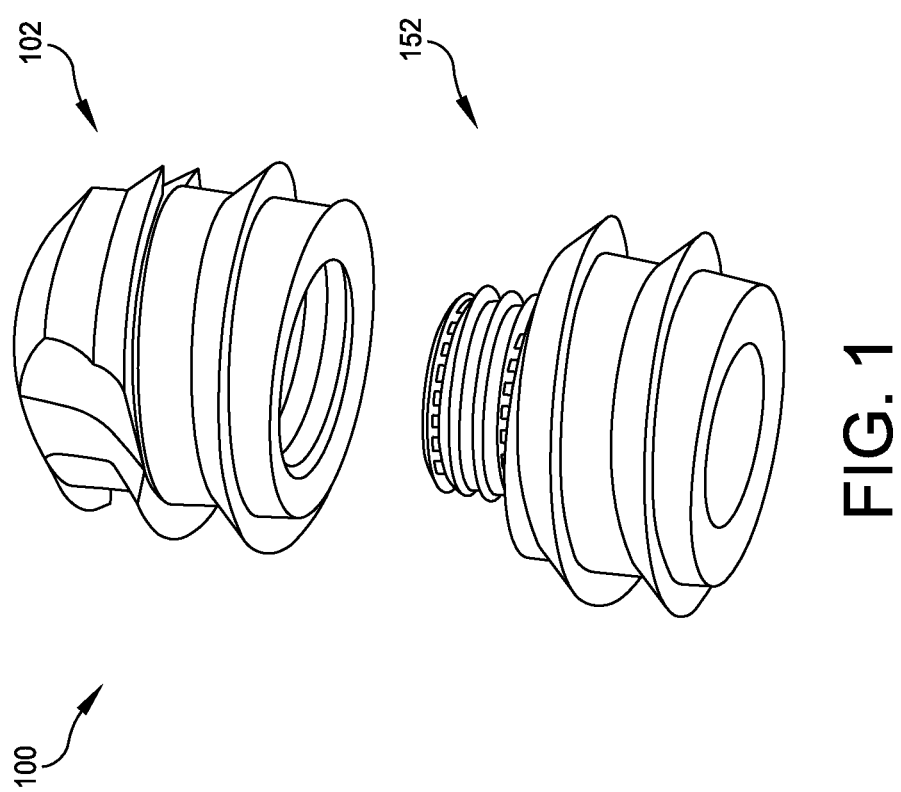
FIG. 1 is an isometric exploded view of one example of a multi-component implant having external fixation in accordance with some embodiments.

This description of the exemplary embodiments is intended to be read in connection with the accompanying drawings, which are to be considered part of the entire written description. The drawing figures are not necessarily to scale, and certain features may be shown exaggerated in scale or in somewhat schematic form in the interest of clarity and conciseness. In the description, relative terms such as "horizontal," "vertical," "up," "down," "top" and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise. When only a single machine is illustrated, the term "machine" shall also be taken to include any collection of machines that individually or jointly execute a set (or multiple sets) of instructions to perform any one or more of the methodologies discussed herein. The term "operatively connected" is such an attachment, coupling or connection that allows the pertinent structures to operate as intended by virtue of that relationship. In the claims, means-plus-function clauses, if used, are intended to cover the structures described, suggested, or rendered obvious by the written description or drawings for performing the recited function, including not only structural equivalents but also equivalent structures.

The disclosed systems and methods provide for enhanced external fixation between an implant and bone. In some embodiments, the implant is a multi-component stem, such as the stem of a total ankle prosthesis. The multiple components may be joined together ex situ or in situ as described herein and as will otherwise be understood by one of ordinary skill in the art. While the following descriptions may reference an ankle prosthesis, such as the INBONE™ Total Ankle System available from the Wright Medical Group and the ankle prostheses disclosed in the '362 Patent, which was incorporated by reference above, it should be understood that the disclosed systems and methods are not to be limited to such prosthesis and may be used in connection with any number of different prosthesis. For example, in some embodiments, the implant may be a multi-component intramedullary nail.

FIG. 1 illustrates one example of an implant 100 having external fixation. Implant 100 includes a first component 102 and a second component 152. Although two components are illustrated, one of ordinary skill in the art will understand that the number of components may be increased (or decreased) to provide an implant of a desired or suitable length. In some embodiments, component 102 is a top or leading component and component 152 is a middle and/or bottom component. Put another way, component 102 may be the first component inserted into an intramedullary canal and form the top end of a stem or prosthesis, and one or more components 152 may be provided to form a stem or prosthesis of differing lengths as described herein. Additionally, the external fixation can be applied to a monolithic stem.

Figure 4:
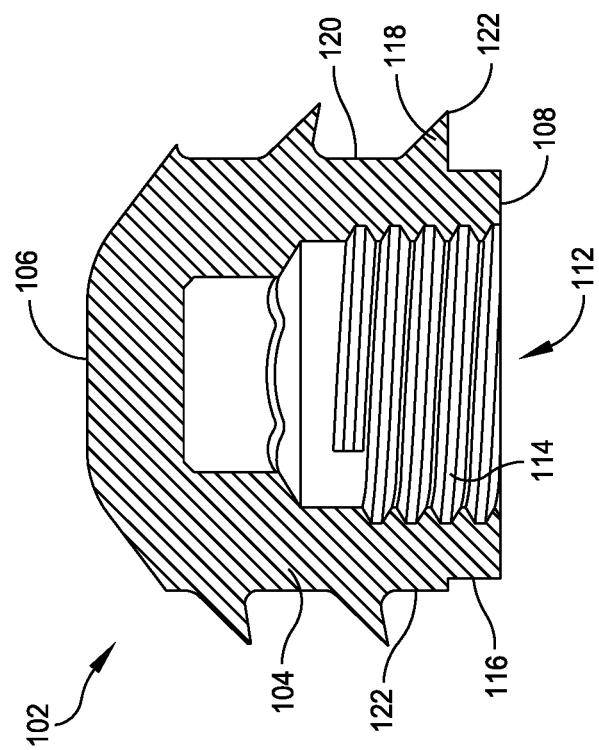
FIG. 4 is a cross-sectional view of the first component illustrated in FIG. 2 in accordance with some embodiments.
Figure 3:
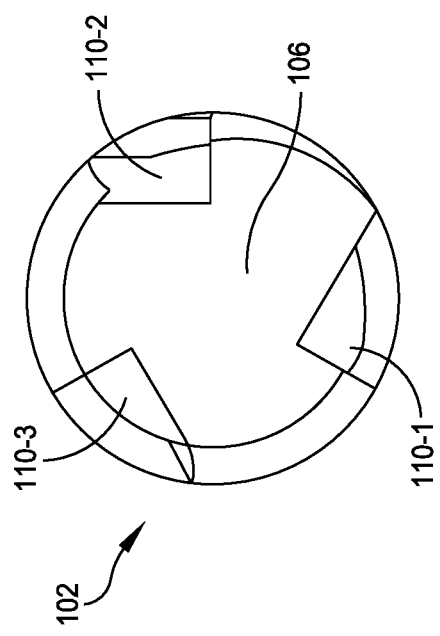
FIG. 3 is a top side view of the first component illustrated in FIG. 2 in accordance with some embodiments.
Figure 2:
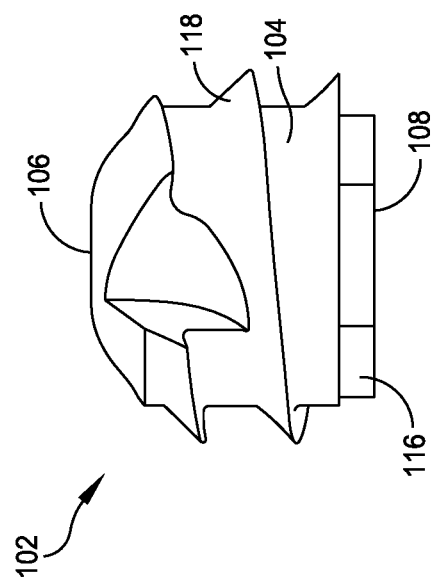
FIG. 2 is a side view of a first component of the multi-component implant having external fixation illustrated in FIG. 1 in accordance with some embodiments.

FIGS. 2-4 provide different views of one example of a component 102. Component 102 has a body 104, which may have a generally cylindrical shape, extending from a first end 106 to a second end 108. End 106 may be a top or leading end and be tapered relative to the rest of body 104 such that end 106 terminates in a blunt end as shown in FIG. 3. In some embodiments, one or more cutting features 110 (e.g., cutting features 110-1, 110-2, 110-3) are formed around the periphery of end 106. Cutting features 110 facilitate insertion of the component into an intramedullary canal and clearing of cancellous bone as will be understood by one of ordinary skill in the art. While three cutting features 110 are illustrated, fewer or more cutting features may be provided about the periphery of end 106. Additionally, the cutting features 110 may be provided symmetrically around end 106 as shown in FIG. 3, or the cutting features 110 may be arbitrarily positioned around end 106.

End 108 may be a trailing or coupling end configured to be engaged by or to engage another prosthesis component. For example, end 108 may include a coupling element 112 as best seen in FIG. 4. In some embodiments, coupling element 112 is a female coupling that includes a threaded hole 114. However, it should be understood that female coupling element 112 may take other forms, such as those female coupling elements described in the '306 Application, which was incorporated by reference in its entirety above. In some embodiments, coupling element 112 is a male coupling element, such as a threaded stem or other male coupling element described in the '306 Application.

In some embodiments, an engagement element 116 is disposed adjacent to end 108 as best seen in FIGS. 2 and 4. Engagement element 116 may be configured to be engaged by a tool, such as a wrench, during the coupling of component 152 to component 102. For example, engagement element may include one or more flats or may include arcuate channels, such as arcuate channels 513 described with reference to FIGS. 22-25 in the '306 Application.

Component 102 also includes one or more external fixation elements 118 disposed on and extending from outer surface 120 of body 104. In the embodiment illustrated in FIGS. 1-4, external fixation element 118 is a single thread that wraps around the outer surface 120 of body 104 such that the outer surface 120 of body forms a trough of the thread 118. The thread may have a constant pitch and thread height (e.g., the distance from the body 104 to the apex or crest 122 of the thread 118) along its length. In some embodiments, the pitch and/or thread height varies along the length of the thread. For example, in some embodiments, the thread height increases (either consistently or intermittently) along the length of the thread such that the thread height adjacent to end 106 is less than a thread height adjacent to end 108. Increasing the thread height would allow the leading end 106 to be inserted into bone with less force while increasing the fixation (and force required to implant the component) between the component and surrounding bone the farther the component is implanted. In some embodiments, the pitch (i.e., distance between adjacent threads) may decrease along the length of the thread. For example, the distance between adjacent crests 122 near end 106 may be greater than a distance between adjacent crests 122 near end 108 to provide a locking function. It should be understood that the height of and distance between crest both may vary along the length of component 102 or just one of the height of or distance between adjacent crests 122 may vary.

Although a single continuous thread is illustrated in FIGS. 1-4, other types of external fixation elements may be provided. For example, the single continuous thread may be replaced by a plurality of interrupted thread segments, which may be formed by making one or more cuts parallel to the longitudinal axis of component 102 as will be understood by one of ordinary skill in the art. Additionally or alternatively, one or more ridges or barbs, such as those described in the '040 Application, may be provided around the circumference of component 102. The ridges or barbs may be arranged symmetrically or randomly around the body 104. For example, the ridges or barbs, which may be angled (e.g., have a wedge shape) to facilitate insertion of component 102 into bone while resisting pulling out or disengagement, may be arranged in rows or columns (e.g., non-helically arranged) or be arranged helically about component 102.

Figure 9:
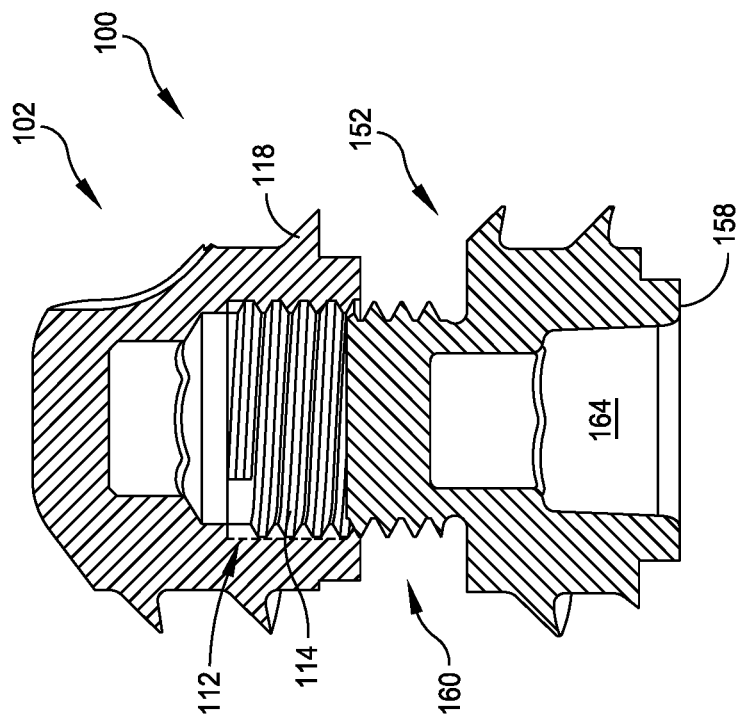
FIG. 9 is a cross-sectional view of the first and second components illustrated in FIG. 8 in accordance with some embodiments.
Figure 8:
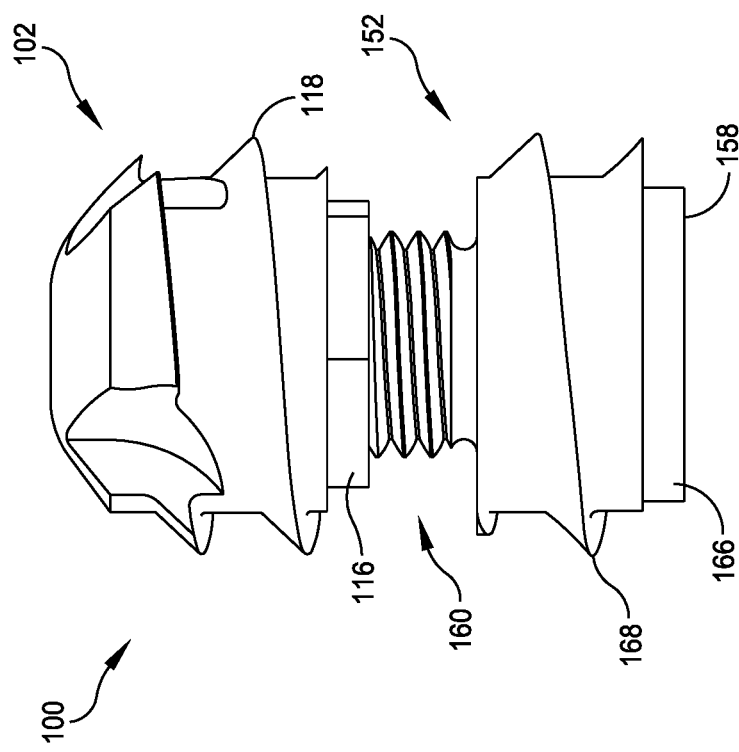
FIG. 8 is a side view of the first and second components being coupled together in accordance with some embodiments.

FIGS. 5-7 provide different views of one example of component 152. Component 150 has a body 154, which may have a generally cylindrical shape, extending from a first end 156 to a second end 158. End 156 may be a top or leading end and include a coupling element 160 for coupling component 152 to another component, such as to component 102 as shown in FIGS. 8 and 9 or to another component 152. In some embodiments, coupling element 160 is a male coupling element comprising a threaded protrusion as illustrated in FIGS. 5 and 6. However, it should be understood that male coupling element 160 may take other forms, such as those male coupling elements described in the '306 Application, which was incorporated by reference in its entirety above. In some embodiments, coupling element 160 is a female coupling element, such as a threaded hole or other female coupling element described in the '306 Application.

End 158 may be a trailing end and configured to be engaged by or to engage another prosthesis component. For example, end 158 may include a coupling element 162 as best seen in FIG. 7. In some embodiments, coupling element 162 is a female coupling that includes a tapered hole 164 (e.g., Morse taper). However, it should be understood that female coupling element 162 may take other forms, such as a threaded hole and those female coupling elements described in the '306 Application, which was incorporated by reference in its entirety above. In some embodiments, coupling element 162 is a male coupling element, such as a threaded stem or other male coupling elements described in the '306 Application.

In some embodiments, an engagement element 166 is disposed adjacent to end 158 as best seen in FIGS. 5 and 7. Engagement element 166 may be configured to be engaged by a tool, such as a wrench, during the coupling of component 152 to component 102. For example, engagement element 166 may include one or more flats or may include arcuate channels, such as arcuate channels 513 described with reference to FIGS. 22-25 in the '306 Application.

Component 152 also includes one or more external fixation elements 168 disposed on and extending from outer surface 170 of body 154. In the embodiment illustrated in FIGS. 5-7, external fixation element 168 is a single thread that wraps around the outer surface 170 of body 154 such that the outer surface 170 of body forms a trough of the thread 168. The thread may have a constant pitch and thread height (e.g., the distance from the body 154 to the apex or crest 172 of the thread 168) along its length. In some embodiments, the pitch and/or thread height varies along the length of the thread. For example, in some embodiments, the thread height increases (either consistently or intermittently) along the length of the thread such that the thread height adjacent to end 156 is less than a thread height adjacent to end 158. Increasing the thread height would allow the leading end 156 to be inserted into bone with less force while increasing the fixation (and force required to implant the component) between the component and surrounding bone the farther the component is implanted. In some embodiments, the pitch (i.e., distance between adjacent threads) may decrease along the length of the thread. For example, the distance between adjacent crests 172 near end 156 may be greater than a distance between adjacent crests 172 near end 168 to provide a locking function. It should be understood that the height of and distance between crest both may vary along the length of component 152 or just one of the height of or distance between adjacent crests 172 may vary. Additionally, the external fixation design although shown as single lead continuous thread can include multiple lead designs to help and ease insertion.

Although a single continuous thread is illustrated in FIGS. 5-7, other types of external fixation elements may be provided. For example, the single continuous thread may be replaced by a plurality of interrupted thread segments, which may be formed by making one or more cuts parallel to the longitudinal axis of component 152 as will be understood by one of ordinary skill in the art. Additionally or alternatively, one or more ridges or barbs, such as those described in the '040 Application, may be provided around the circumference of component 152. The ridges or barbs may be arranged symmetrically or randomly around the body 154. For example, the ridges or barbs, which may be angled (e.g., have a wedge shape) to facilitate insertion of component 152 into bone while resisting pulling out or disengagement, may be arranged in rows or columns (e.g., non-helically arranged) or be arranged helically about component 152.

In some embodiments, the external fixation elements 118, 168 of components 102, 152 are configured to provide a single, continuous external fixation element. For example, in embodiments in which external fixation elements 118, 168 are implemented as a single continuous thread or include a plurality of thread segments, the threads 11, 168 may be aligned with one another when components 102, 152 are coupled together such that crest 122 of external fixation element 122 transitions to crest 172 of fixation element 168 and appear as a single continuous crest. In such embodiments, fixation element 168 may have the same pitch and thread height as fixation element 118, including when the pitch and/or thread height of fixation element 118 varies along its length. For example, fixation element 168 may be configured to vary at the same rate (e.g., change in pitch and/or height) as the rate at which fixation element 118 changes along its length. However, it is also contemplated that one of fixation elements 118, 168 may vary (e.g., pitch and/or thread height) while the other is constant while still providing a continuous transition from one component to another.

In some embodiments, the external fixation elements 118, 168 of components 102, 152 are different from one another and/or do not transition continuously from one component to another. For example, external fixation element 118 may be implemented as a single continuous thread having a first pitch and a first thread height, and external fixation element 168 may be implemented as a single continuous thread having a second pitch and a second thread height. In another example, external fixation element 118 may be implemented as a thread having a plurality of thread segments, and external fixation element 168 may be implemented as a plurality of ridges or barbs.

The use of the external fixation elements described above advantageously increases the amount of fixation between component 152 and surrounding bone, which can obviating the need to provide a plasma spray or other coating on component 102 Eliminating the step of plasma spraying component 102 reduces the complexity of the manufacturing process and also reduces the cost to produce the component. However, it should be understood that external fixation elements may be used in conjunction with plasma spray coating or other surface texturing/roughing techniques, including surface treatment techniques that promote bone ingrowth. An example of such a surface coating is the porous metallic material sold by Wright Medical Technology under the name ADAPTIS™, although other suitable treatments or coatings may be used as will be understood by one of ordinary skill in the art.

Figure 11:
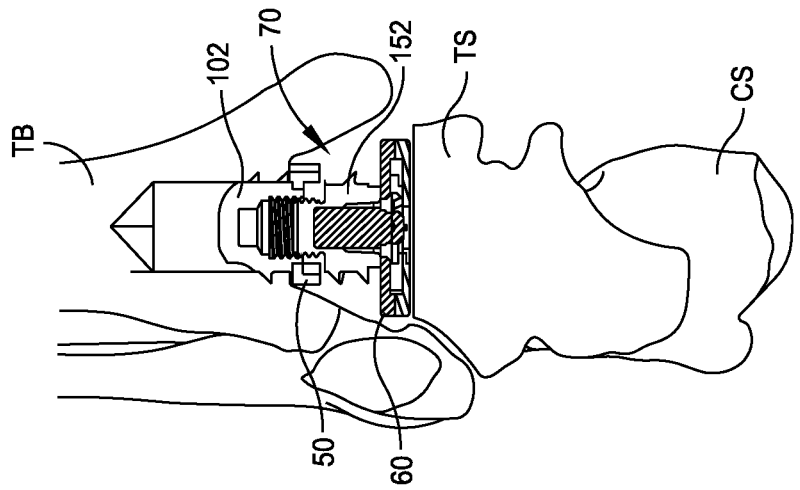
FIG. 11 is a cross-sectional view of a multi-component prosthesis being implanted via an anterior approach in accordance with some embodiments.
Figure 10:
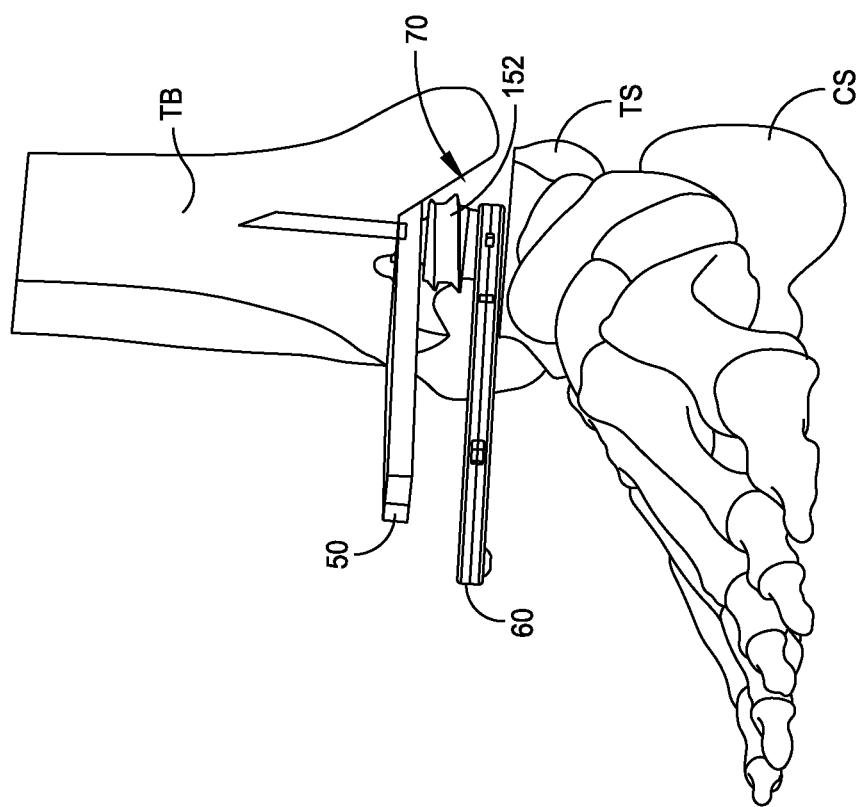
FIG. 10 illustrates one example of a multi-component prosthesis being implanted via an anterior approach in accordance with some embodiments.

As noted above, while two components are illustrated, it should be understood that fewer or additional components may be provided. The components may be coupled together ex situ or in situ. For example, FIGS. 10 and 11 are schematic illustrations of a multi-component implant—taking the form of a tibial stem—being installed in an intramedullary canal via an anterior approach. One example of such an approach is described in detail in the '561 Patent, which was incorporated by reference above. Briefly, once an anterior opening has been created, the first component 102 may be inserted into an intramedullary canal formed in the bone, which may be a tibia TB. The insertion of component 102 may be facilitated by engagement element 116 being engaged by a first tool 50, such as a wrench, as shown in FIGS. 10 and 11. The wrench 50 may be used to rotate component 102 (FIG. 11), which is then advanced into the intramedullary canal due to the engagement between the bone and external fixation element 118. One of ordinary skill in the art will understand that other tool(s) may be used to insert component 102 into an intramedullary passage. For example, depending on the type of external fixation element(s) 118 provided on the body 104, a hammer-like device (e.g., a slide/slap hammer) may be used to insert component 102 when the external fixation element includes one or more ridges or barbs are provided.

A second component 152 may be coupled to the first component 102. For example, the coupling element 112 of component 102 may be engaged by coupling element 160 of component 152. In some embodiments, component 102 and component 152 are coupled together ex situ prior to inserting components 102 and 152 into the intramedullary canal or channel. In some embodiments, component 102 and component 152 may be coupled to each other in situ. For example, component 102 may be inserted into a canal or channel formed bone via the anterior opening formed in bone, and then component 152 may be coupled to component 102 via the anterior opening 70. As shown in FIGS. 10 and 11, a second tool 60, which may be another wrench, may be used to engage the engagement feature 166 of component 152 while the first tool 50 continues to engage engagement element 116 of component 102 to permit component 152 to rotate relative to component 102.

Figure 14:
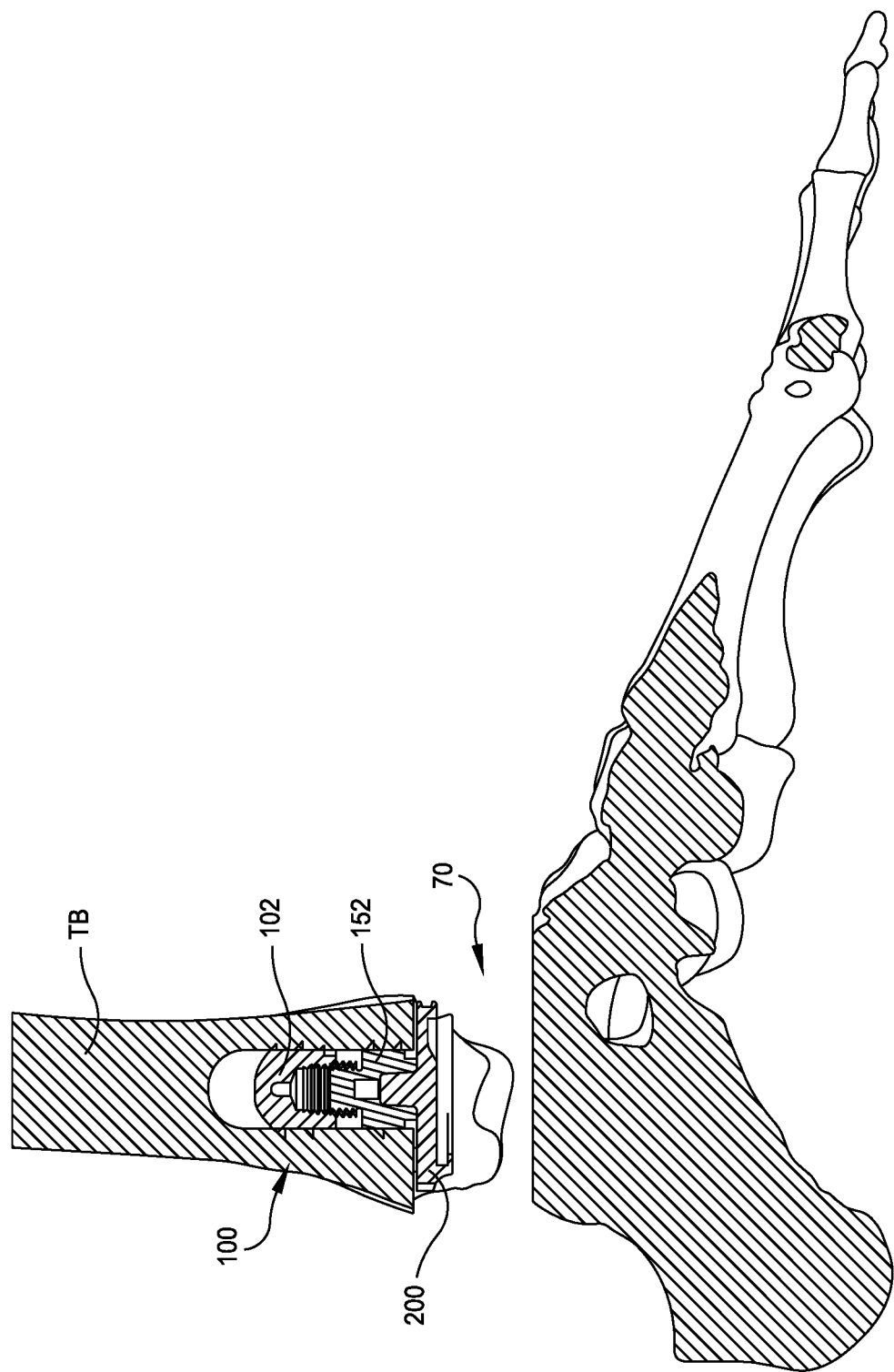
FIG. 14 is a cross-sectional view of a multi-component prosthesis implanted in a patient in accordance with some embodiments.

One or more additional components may be coupled to component 152. For example, depending on the desired length of the stem, another component 152 may be coupled to component 152. In some embodiments, a tibial tray, such as a tibial tray described in any one of the '040 Application, the '306 Application, the '362 Patent, and the '561 Patent may be coupled to component 152. FIG. 14 illustrates one example of a tibial tray 200 coupled to a stem 100 comprising components 102, 152 in accordance with some embodiments.

Figure 13:
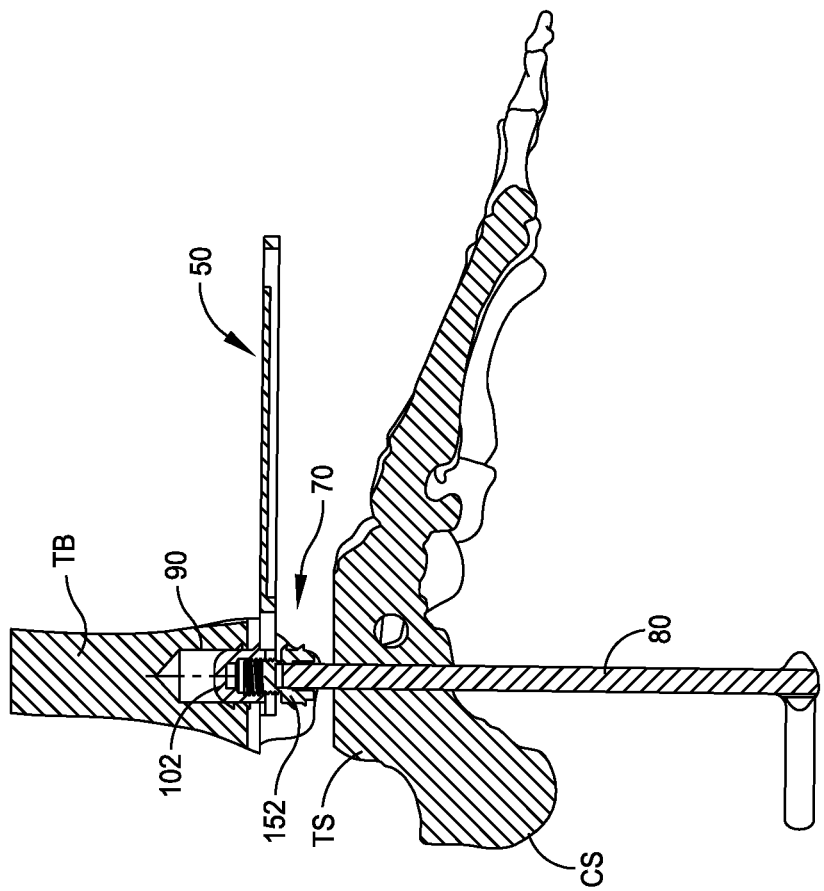
FIG. 13 is a cross-sectional view of a multi-component prosthesis being implanted via a plantar approach in accordance with some embodiments.
Figure 12:
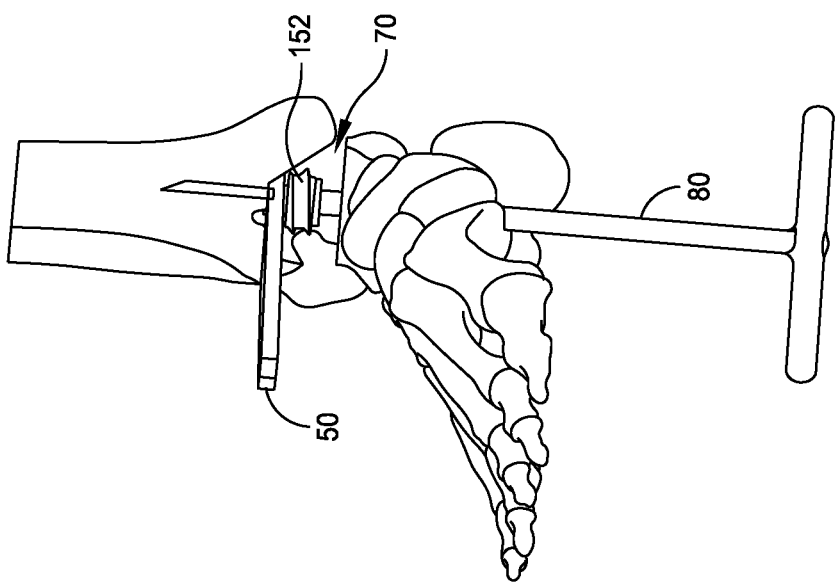
FIG. 12 illustrates one example of a multi-component prosthesis being implanted via a plantar approach in accordance with some embodiments.

FIGS. 12 and 13 illustrate one example of a system 100 being implanted via a plantar approach in accordance with some embodiments. One example of such an approach is described in detail in the '362 Patent (see, e.g., FIGS. 29A-30 and corresponding descriptions), which was incorporated by reference above. Briefly, once an anterior opening has been created and a hole has been established through the calcaneus CS and/or talus TS, the first component 102 may be inserted into an intramedullary canal formed in the bone, which may be a tibia TB. In some embodiments, component 102 is inserted into the anterior opening 70 (e.g., resected joint spaced) formed between the tibia TB and talus TS. The insertion of component 102 may be facilitated by engagement element 116 and coupling element 112 being engaged by tools 50, 80, as shown in FIGS. 12 and 13. For example, driving tool 80 may be received within coupling element 112 of component 102 and then used to advance component 112 into the intramedullary channel 90 formed in tibia TB. Engagement element 116 may then be engaged by tool 50 and tool 80 may be disengaged from coupling element 112.

Coupling element 160 of component 152 may be brought into engagement with coupling element 112 as engagement element 116 is engaged by tool 50. Tool 80 is received within coupling element 162 and then used to coupled component 152 to component 102 as tool 50 engages engagement element 116 to prevent component 102 from rotating as component 152 is rotated by tool 80.

One or more additional components may be coupled to component 152 once components 102 and 152 are coupled together. For example, depending on the desired length of the stem, another component 152 may be coupled to component 152. In some embodiments, a tibial tray, such as a tibial tray described in any one of the '040 Application, the '306 Application, the '362 Patent, and the '561 Patent may be coupled to component 152. As described above, FIG. 14 illustrates one example of a tibial tray 200 coupled to a stem 100 comprising components 102, 152 in accordance with some embodiments.

The disclosed systems and methods advantageously utilize modular components with external fixation that provides increased fixation between the resulting implant and surrounding bone while at the same time providing flexible methods of installation. Further, by providing external fixation elements as discussed herein, the number and complexity of manufacturing and/or processing steps may be reduced (e.g., complex and costly steps such as plasma spray may be eliminated). Of course, such steps may also be provided and work in combination with the fixation elements described herein.

In some embodiments, an apparatus includes a body extending from a first end to a second end. The first end is a leading end, and the second end includes a first coupling element configured to couple the body to a first other component. The body includes an external fixation element extending along a length of the first component. The external fixation element is configured to engage bone.

In some embodiments, the external fixation element includes a thread.

In some embodiments, the thread has a pitch and a thread height, and wherein at least one of the pitch and the thread height varies along the length of the first component.

In some embodiments, the pitch of the thread is greater adjacent to the first end than adjacent to the second end.

In some embodiments, the height of the thread is greater adjacent to the second end than adjacent to the first end.

In some embodiments, the thread includes a plurality of thread segments.

In some embodiments, each thread segment includes a respective thread lead.

In some embodiments, the fixation element includes a plurality of ridges.

In some embodiments, the plurality of ridges are arranged in rows and columns along the body.

In some embodiments, the body includes an engagement element disposed adjacent to the second end.

In some embodiments, the first end includes a cutting element.

In some embodiments, the first end includes a plurality of cutting elements.

In some embodiments, the first end includes a second coupling element, and the second coupling element is configured to couple the body to a second other component.

In some embodiments, the body is the body of a monolithic stem, and the first other component includes a tibial tray.

In some embodiments, the external fixation element includes multiple thread leads.

In some embodiments, a system includes a first component and a second component. The first component includes a first body having a first length extending from a first end to a second end. The first end is a leading end, and the second end includes a first coupling element. The second component includes a second body having a second length extending from a third end to a fourth end. The third end includes a second coupling element, and the fourth end including a third coupling element. At least one of the first body and the second body includes a first external fixation element configured to engage bone. The second coupling element is configured to be coupled to the first coupling element to couple the first and second components together.

In some embodiments, the first external fixation element includes a thread.

In some embodiments, the thread has a pitch and a thread height. At least one of the pitch and the thread height varies along the length of the first component.

In some embodiments, the pitch of the thread is greater adjacent to the first end than adjacent to the second end.

In some embodiments, the height of the thread is greater adjacent to the second end than adjacent to the first end.

In some embodiments, the thread includes a plurality of thread segments.

In some embodiments, the fixation element includes a plurality of ridges.

In some embodiments, the plurality of ridges are arranged in rows and columns along the body.

In some embodiments, the first body includes the first external fixation element and the second body includes a second external fixation element.

In some embodiments, the first external fixation element includes a first thread having a first pitch and a first height, and the second external fixation element includes a second thread having a second pitch and a second height.

In some embodiments, the first pitch is equal to the second pitch, and wherein the first height is equal to the second height.

In some embodiments, the first pitch is different from the second pitch, and wherein the first height is equal to the second height.

In some embodiments, the first pitch is equal to the second pitch, and the first height is different from the second height.

In some embodiments, the first pitch is different from the second pitch, and wherein the first height is different from the first pitch.

In some embodiments, the first pitch varies along a length of the first component, and wherein the second pitch varies along a length of the second component.

In some embodiments, the first pitch and the second pitch vary at an equal rate.

In some embodiments, the first height varies along a length of the first component, and the second height varies along a length of the second component.

In some embodiments, the first height and the second height vary at an equal rate.

In some embodiments, the first fixation element includes a thread, and the second external fixation element includes a plurality of ridges.

In some embodiments, the first fixation element includes a plurality of ridges, and the second fixation element includes a thread.

In some embodiments, a method includes coupling a first coupling element provided by a first component to a second coupling element provided by a second component to couple together the first component and the second component, and inserting the first component and the second component into an intramedullary channel formed in bone such that an external fixation element extending from a body of at least the first component or the second component engages bone to fix the first component and the second component within the bone.

In some embodiments, the bone is a tibia, and the first component and the second component are inserted through an anterior opening formed in the tibia.

In some embodiments, a method includes coupling a third component to the second component.

In some embodiments, the third component includes a tibial tray.

In some embodiments, the third component includes another component of a tibial stem.

In some embodiments, the first component and second component are coupled together ex situ.

In some embodiments, a method includes inserting a first component into a channel formed in a first bone such that a first external fixation element extending from a body of the first component engages bone, and coupling a second component to the first component in situ by engaging a first coupling element provided by the first component with a second coupling element provided by the second component.

In some embodiments, the second component includes a second external fixation element extending from a body of the second component.

In some embodiments, the bone is a tibia, and the first component and the second component are coupled together in an anterior opening formed in the tibia.

In some embodiments, a method includes coupling a third component to the second component.

In some embodiments, the third component includes a tibial tray.

In some embodiments, the third component includes another component of a tibial stem.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. An apparatus, comprising:
a body extending from a first end to a second end, the first end being a leading end that terminates in a blunt end and includes a plurality of cutting features provided symmetrically around the first end, and the second end including a first coupling element configured to couple the body to a first other component, wherein:

the body includes an external fixation element extending along a length of a first component, the external fixation element configured to engage bone;
the external fixation element includes a thread;
the first coupling element defines a threaded hole that includes a flat surface at an end of the threaded hole;
the thread has a first pitch and a first height;
the threaded hole has a second pitch and a second height;
the first pitch is different from the second pitch;
the first height is different from the second height.

2. The apparatus of claim 1, wherein at least one of the first pitch and the first height varies along the length of the first component.

3. The apparatus of claim 2, wherein the first pitch of the thread is greater adjacent to the first end than adjacent to the second end.

4. The apparatus of claim 2, wherein the first height of the thread is greater adjacent to the second end than adjacent to the first end.

5. The apparatus of claim 1, wherein the thread includes a plurality of thread segments.

6. The apparatus of claim 5, wherein each thread segment includes a respective thread lead.

7. The apparatus of claim 1, wherein the external fixation element includes a plurality of ridges.

8. The apparatus of claim 7, wherein
the plurality of ridges are arranged in rows and columns along the body.

9. The apparatus of claim 1, wherein the body includes an engagement element disposed adjacent to the second end.

10. The apparatus of claim 9, wherein the engagement element includes a flat surface.

11. The apparatus of claim 1, wherein the first end includes a second coupling element, the second coupling element configured to couple the body to a second other component.

12. The apparatus of claim 1, wherein the body is the body of a monolithic stem, and wherein the first other component includes a tibial tray.

13. The apparatus of claim 1, wherein the external fixation element includes multiple thread leads.

14. A system, comprising:
a first component including a first body, the first body having a first length extending from a first end to a second end, the first end being a leading end and the second end including a first coupling element; and
a second component including a second body, the second body having a second length extending from a third end to a fourth end, the third end including a second coupling element, and the fourth end including a third coupling element, wherein:
at least one of the first body and the second body includes a first external fixation element configured to engage bone,
the second coupling element is configured to be coupled to the first coupling element to couple the first and second components together,
the first external fixation element includes a first external thread,
the first coupling element defines a threaded hole,
the first external thread has a first pitch and a first external height,
the threaded hole has an internal pitch and an internal height,
the first external pitch is different from the internal pitch, and the first external height is different from the internal height.

15. The system of claim 14, wherein at least one of the first external pitch and the first external height varies along the length of the first component.

16. The system of claim 15, wherein the first external pitch of the first external thread is greater adjacent to the first end than adjacent to the second end.

17. The system of claim 15, wherein the first external height of the first external thread is greater adjacent to the second end than adjacent to the first end.

18. The system of claim 14, wherein
the first external thread includes a plurality of thread segments, and
the first external fixation element includes a plurality of ridges arranged in rows and columns along the first body.

19. The system of claim 14, wherein the first body includes the first external fixation element and the second body includes a second external fixation element such that the second external fixation element includes a second external thread having a second external pitch and a second external height.

20. The system of claim 19, wherein the first external pitch is equal to the second external pitch, and wherein the first external height is equal to the second external height.

21. The system of claim 19, wherein the first external pitch is different from the second external pitch, and wherein the first external height is equal to the second external height.

22. The system of claim 19, wherein the first external pitch is equal to the second external pitch, and wherein the first external height is different from the second external height.

23. The system of claim 19, wherein the first external pitch is different from the second external pitch, and wherein the first external height is different from the first external pitch.

24. The system of claim 19, wherein the first external pitch varies along a length of the first component, and wherein the second external pitch varies along a length of the second component.

25. The system of claim 24, wherein the first external pitch and the second external pitch vary at an equal rate.

26. The system of claim 19, wherein the first external height varies along a length of the first component, and wherein the second external height varies along a length of the second component.

27. The system of claim 26, wherein the first external height and the second external height vary at an equal rate.

28. The system of claim 14, wherein:
the first body includes the first external fixation element and the second body includes a second external fixation element; and
the second external fixation element includes a plurality of ridges.

29. The system of claim 14, wherein:
the first body includes the first external fixation element and the second body includes a second external fixation element; and
the first fixation element includes a plurality of ridges, and wherein the second fixation element includes a second external thread.

30. The system of claim 14, wherein the third coupling element is a hole including a Morse taper.

* * * * *